US00PP20832P2

(12) United States Plant Patent
Bradford

(10) Patent No.: US PP20,832 P2
(45) Date of Patent: Mar. 16, 2010

(54) INTERSPECIFIC TREE NAMED 'BLACKRED IV'

(50) Latin Name: ***Prunus* sp.**
Varietal Denomination: Blackred IV

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,596

(22) Filed: Dec. 15, 2008

(51) Int. Cl.
*A01H 5/00* (2006.01)

(52) U.S. Cl. ..... Plt./180

(58) Field of Classification Search ..... Plt./180, Plt./184, 186
See application file for complete search history.

(56) References Cited

U.S. PATENT DOCUMENTS

PP7,503 P 4/1991 Bradford
PP13,476 P2 1/2003 Bradford

*Primary Examiner*—June Hwu

(57) ABSTRACT

The present invention relates to an interspecific tree and more particularly to a new and distinct variety broadly characterized by a medium size, moderately vigorous, hardy, and medium productive tree. Being self-unfruitful, the present variety requires cross pollination from an apricot, interspecific, or plum that blooms during the early season. The fruit matures under the ecological conditions described during late June, with the first picking on Jun. 26, 2008. The fruit is uniformly medium to large in size, dark blackish red in skin color, clingstone in type, oblate in shape, mostly red and orange in flesh color, firm in texture, and an excellent balance of acidic and sugar in flavor.

1 Drawing Sheet

Botanical classification: *Prunus* sp.
Varietal denomination: 'Blackred IV'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred IV'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing 'Purple Majesty' plum (U.S. Plant Pat. No. 7,503) was crossed by me in this manner. To pollinate this plum, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H1 15P". They were grown as seedlings on their own root in my greenhouse and upon reaching dormancy transplanted to a cultivated area of my experimental orchard located near Le Grand, Calif. in Merced County (San Joaquin Valley). During the spring of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Purple Majesty' plum by being self-unfruitful and by producing fruit that is dark red to purple in skin color, firm in texture, oblate in shape, clingstone in type, and matures in the second half of June, but is distinguished therefrom by producing fruit that is sweeter in flavor, larger in size, and mostly red in flesh color instead of orange yellow.

The present variety is similar to 'YUMMYROSA' plum (U.S. Plant Pat. No. 13,476) by producing fruit that is dark red in skin color, mostly oblate in shape, and matures in late June, but is distinguished therefrom by producing fruit that is firmer in texture, that is larger in size, that will hang longer on the tree before dropping or softening, that does not have green shoulders, and that is fully red to orange in flesh color instead of primarily yellow with just a thin red ring near the skin.

SUMMARY OF VARIETY

The present interspecific variety is characterized by a medium size, moderately vigorous, hardy, and medium productive tree. Being self-unfruitful, the present variety requires cross pollination from an apricot, interspecific, or plum that blooms during the early season. The fruit matures under the ecological conditions described during late June, with the first picking on Jun. 26, 2008. The fruit is uniformly medium to large in size, dark blackish red in skin color, clingstone in type, oblate in shape, mostly red and orange in flesh color, firm in texture, and an excellent balance of acidic and sugar in flavor.

DRAWING

The accompanying photograph consists of four whole fruits positioned to display the characteristics of the skin color and form, one half of a fruit divided transversely to the suture plane to reveal the flesh and stone, a freshly cleaned stone, a young tip shoot growth, typical leaves, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of shipping ripe on Jun. 27, 2008, on the original tree during its seventh growing season. The flower and bud descriptions were developed during the previous blooming season. All major color code designations are by reference to the Inter-Society Color Council, National Bureau of Standards. Common color names are also used.

Parentage

Seed parent: 'Purple Majesty' (U.S. Plant Pat. No. 7,503).
Pollen parent: Unknown.

Tree

Size: Medium, reaching and maintaining a height of 10' [3.05 m.] and a spread of 10' [3.05 m.] after seven growing seasons utilizing typical dormant pruning.
Vigor: Moderately vigorous, responding typically to irrigation and fertilization. The variety grows about 4' [1.22 m.] of surplus top-growth during the spring and summer. The plant should be grown on a standard commercial rootstock for production purposes.
Growth: Spreading and open.
Form: Pruned to a Perpendicular V type.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Medium production, thinning usually necessary.
Fertility: Self-unfruitful, requiring cross pollination by a suitable early seasonal blooming apricot, interspecific, or plum, such as 'Plumsweetone' plum (U.S. Plant Pat. No. 14,219).
Bearing: Regular bearer, weather dependent.
Trunk:
- *Size.*—Medium, reaching a maximum diameter of 4½" [114 mm.] after the seventh growing season.
- *Texture.*—Medium shaggy.
- *Bark color.*—A Grayish brown [61. gy.Br] and Grayish yellowish brown [80. gy.yBr] variegation with Light yellowish brown [76. l.yBr] crevices present.
- *Lenticels.*—Approximate Number Per Square Inch: 5. Color: Strong brown [55. s.Br]. Average Size: ⅜" [9.5 mm.]. Shape: Eye-shaped, elongated.

Branches:
- *Size.*—Limb diameter is 2⅝" [66.7 mm.] measured 12" above the crotch, 1½" [38.1 mm.] measured 12" above the first fork.
- *Texture.*—Smooth on first year wood, increasing roughness with age.
- *Color.*—1st Year Wood Topside: Strong yellowish brown [74. s.yBr]. 1st Year Wood Underside: Very yellow green [115. v.YG]. 2nd Year Wood: A Dark grayish brown [62. d.gy.Br] and Brownish orange [54. brO] variegation with Deep brown [56. deep Br] crevices present. Older Wood: Similar to the trunk color.
- *Lenticels.*—Number Per Square Inch: More than 80 on second year wood. Color: Strong orange yellow [68. s.OY]. Average Size: 1/64" [0.4 mm.]. Shape: Elongated, eye shaped.

Leaves:
- *Size.*—Large. Average Length: 4½" [114.3 mm.]. Average width: 1 15/16" [49.2 mm.].
- *Arrangement.*—Alternate.
- *Thickness.*—Medium.
- *Form.*—Elliptical.
- *Apex.*—Acuminate.
- *Base.*—Acute with an average base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: 7/16" [11.1 mm.]. Average Thickness: 1/16" [1.6 mm.]. Color: Brilliant yellow green [116. brill.YG].
- *Stipules.*—Number: 2 per leaf, up to 6 per growing tip. Average Length: 7/16" [11.1 mm.]. Color: Brilliant yellow green [116. brill.YG] becoming Light brown [57. l.Br] with age.
- *Glands.*—Number: Mostly 2 to 3 per leaf. Position: Most alternately, some oppositely, positioned on the petiole and the base of the leaf blade. Size: Small. Form: Globose. Color: Brilliant yellow green [116. brill.YG] acquiring a Grayish reddish brown [46. gy.rBr] center with age. Leaf buds: Pointed, medium.

Flower buds:
- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, about thirty stamens, five sepals and petal locations alternately positioned.
- *Average flower diameter.*—1" [25.4 mm.].
- *Number of petals.*—Five, no double blossoms observed.
- *Petal shape.*—Oval to circular.
- *Petal margin.*—Entire, somewhat wavy with notches typical.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White] on both sides.
- *Anther color.*—Strong yellow [84. s.Y].
- *Stigma color.*—Brilliant greenish yellow [98. brill.gY].
- *Sepal color.*—Brilliant yellow green [116. brill.YG] on the outer surface.
- *Sepal length.*—⅛" [3.2 mm.].
- *Sepal width.*—⅛" [3.2 mm.].
- *Sepal apex.*—Rounded to elliptical to match the width and length.
- *Sepal margin.*—Fairly smooth to the naked eye, slightly serrate toward the apex when magnified.
- *Average pistil length.*—11/16" [17.5 mm.], longer than normal.
- *Average stamen length.*—½" [12.7 mm.].
- *Fragrance.*—Moderate.

*Pollen production.*—Abundant, bee enticing.
*Bloom density.*—Heavy.
*Number per cluster.*—2 to 10, average 4.
*Blooming period.*—Early, one day after 'Ambra' (unpatented).
*Onset of bloom.*—One percent on Feb. 22, 2008.
*Date of full bloom.*—Mar. 1, 2008.
*Duration of bloom.*—One to two weeks, dependent on ambient temperature.

FRUIT

Maturity when described: Shipping ripe, Jun. 27, 2008.
Date of first picking: Jun. 26, 2008.
Date of last picking: Jul. 5, 2008.
Size: Uniform, medium to large.
*Average diameter axially.*—2¼" [57.2 mm.].
*Average diameter across cheek plane.*—2¾" [69.9 mm.].
*Average diameter across suture plane.*—2 11/16" [68.3 mm.].
*Typical weight.*—5.2 ounces [147 grams].
Form: Uniform, oblate, symmetrical.
*Longitudinal section form.*—Oblate.
*Transverse section through axial diameter.*—Round.
Suture: A shallow groove or trough extending from the base to the apex, ending in a marked depression just beyond pistol point.
Ventral surface: Rounded.
Lips: Virtually no lips.
Cavity: Flaring, circular, stem markings generally not present.
*Depth.*—7/16" [11.1 mm.].
*Breadth.*—1 1/16" [27 mm.].
Base: Truncate.
Apex: Truncate.
Pistil point: An inconspicuous Light grayish brown [60. l.gy.Br] dot.
Stem: Medium.
*Average length.*—½" [12.7 mm.].
*Average width.*—3/32" [2.4 mm.].
Skin:
*Thickness.*—Medium.
*Surface.*—Smooth.
*Tenacity.*—Tenacious to the flesh.
*Astringency.*—Slight.
*Tendency to crack.*—Non observed in dry season.
*Color.*—Blackish red [21. blackish R] over a Dark red [16. d.R] background with very small Light brown [57. l.Br] freckles throughout. The fruit also has Light brown [57. l.Br] concentric markings on the shoulders around the stem.
*Bloom.*—Abundant.
Flesh:
*Color.*—Deep red [13. deep R] near the skin, Strong reddish orange [35. s.rO] toward the stone.
*Surface of pit cavity.*—Covered with Strong pink [2. s.Pk] broken fibers when twisted from the stone.
*Amygdalin.*—Moderate.
*Juice.*—Moderate, rich.
*Texture.*—Firm, tough, meaty.
*Fibers.*—Abundant, fine, tender.
*Ripens.*—Slightly earlier toward the apex.
*Flavor.*—A tasty blend of acid and sugar, typically 17 brix.
*Aroma.*—Very slight.
*Eating quality.*—Excellent.

STONE

Type: Clingstone.
Form: Oval.
Hilum: Narrow to oblong.
Base: Notched to somewhat cordate.
Apex: Rounded, with a sharp 1/16" [1.6 mm.] tip.
Sides: Equal.
Surface: Rough throughout with a few irregular ridges on both sides of the dorsal fin.
External color of stone: Light brown [57. l.Br].
Pit wall color when cracked: Pale orange yellow [73. p.OY].
Cavity surface color: Moderate orange yellow [71. m.OY].
Average pit wall thickness: 1/16" [1.6 mm.].
Average width: ⅞" [22.2 mm.].
Average length: 15/16" [23.8 mm.].
Average breadth: ⅜" [9.5 mm.].
Tendency to split: Slight.
Kernel:
*Form.*—Oval.
*Skin color.*—Pale yellow [89. p.Y] when first removed becoming Brownish orange [54. brO] when dry.
*Pellicle color.*—Grayish yellow [90. gy.Y].
*Vein color.*—Grayish yellow [90. gy.Y].
*Taste.*—Bitter.
*Viable.*—Yes.
*Average width.*—7/16" [11.1 mm.].
*Average length.*—½" [12.7 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'YUMMYROSA' plum (U.S. Plant Pat. No. 13,476) by producing fruit that is dark red to purple in skin color, mostly oblate in shape, and matures in late June, but is distinguished therefrom by producing fruit that is firmer in texture, that is larger in size, that will hang longer on the tree before dropping or softening, that does not have green shoulders, and that is fully red to orange in flesh color instead of primarily yellow with just a thin red ring near the skin.

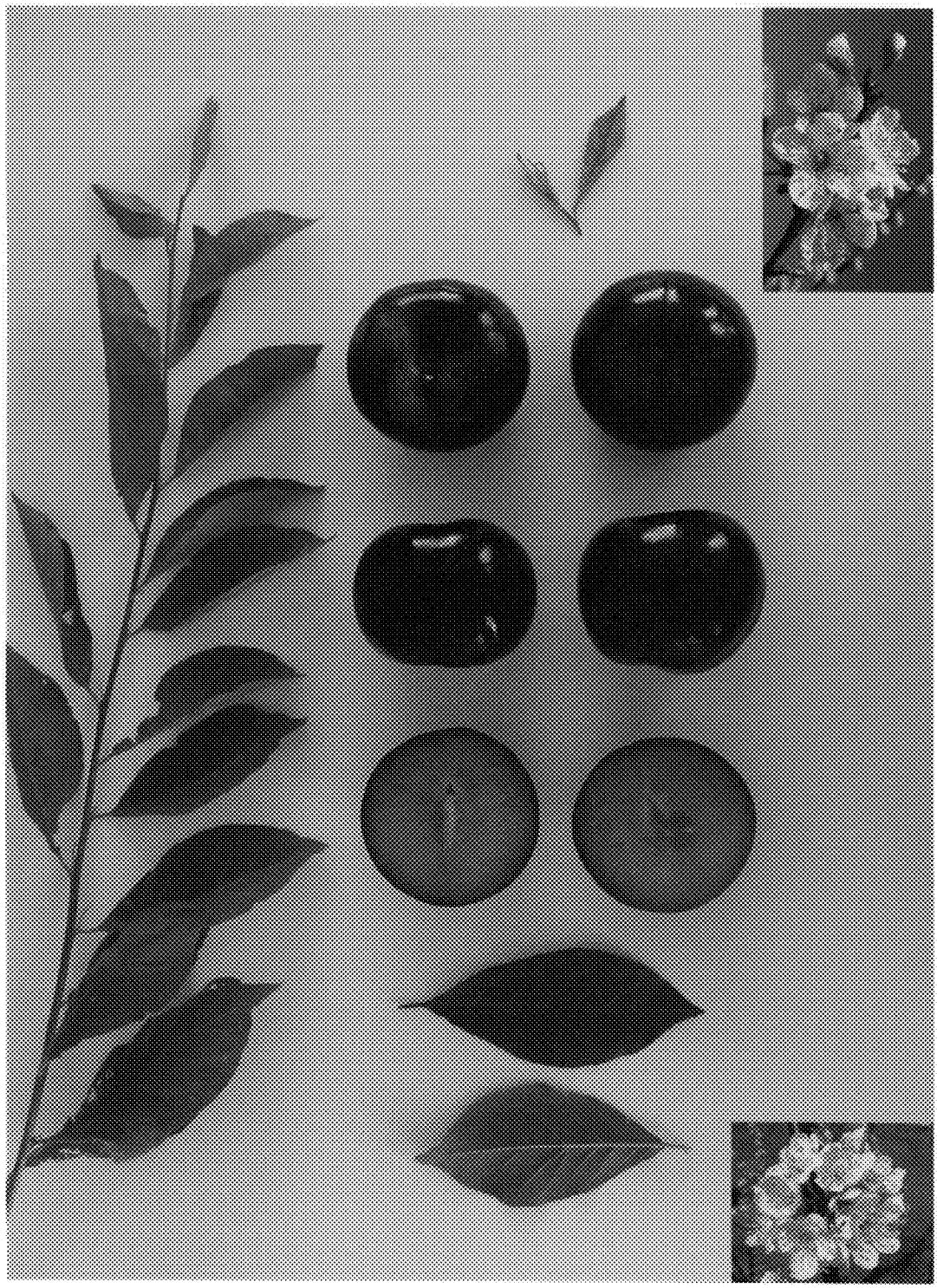

* * * * *